(12) United States Patent
Choi

(10) Patent No.: US 8,968,774 B2
(45) Date of Patent: Mar. 3, 2015

(54) PREPARATION AND COMPOSITION OF MELOXICAM TRANSDERMAL DRUG DELIVERY SYSTEM

(75) Inventor: Hoo-Kyun Choi, Gwangji (KR)

(73) Assignees: Industry-Academic Cooperation Foundation, Chosun University, Gwangju (KR); Golden Pacific Bio Limited, Hong Kong (CN)

( * ) Notice: Subject to any disclaimer, the term of this patent is extended or adjusted under 35 U.S.C. 154(b) by 375 days.

(21) Appl. No.: 12/442,550

(22) PCT Filed: Sep. 20, 2007

(86) PCT No.: PCT/KR2007/004569
§ 371 (c)(1),
(2), (4) Date: Mar. 24, 2009

(87) PCT Pub. No.: WO2008/038939
PCT Pub. Date: Apr. 3, 2008

(65) Prior Publication Data
US 2009/0246266 A1    Oct. 1, 2009

(30) Foreign Application Priority Data

Sep. 27, 2006 (KR) ........................ 10-2006-0094007

(51) Int. Cl.
*A61K 9/70* (2006.01)
*A61K 31/5415* (2006.01)

(52) U.S. Cl.
CPC ............ *A61K 9/7061* (2013.01); *A61K 31/5415* (2013.01)
USPC .......................................... 424/449; 424/443

(58) Field of Classification Search
None
See application file for complete search history.

(56) References Cited

U.S. PATENT DOCUMENTS

| 4,746,509 A * | 5/1988 | Haggiage et al. ............. 424/449 |
| 5,916,587 A * | 6/1999 | Min et al. ...................... 424/448 |
| 2006/0110434 A1 * | 5/2006 | Yamaguchi et al. .......... 424/448 |
| 2007/0275943 A1 * | 11/2007 | Morgan et al. ................ 514/182 |

FOREIGN PATENT DOCUMENTS

| KR | 10-2000-0018965 A | 4/2000 |
| KR | 10-2000-0047908 A | 7/2000 |
| KR | 10-2003-0000341 A | 1/2003 |
| KR | 10-2006-0049598 A | 5/2006 |
| KR | 10-2006-0059365 A | 6/2006 |
| WO | 2005/123046 A1 | 12/2005 |
| WO | WO 2005123046 A1 * | 12/2005 |

OTHER PUBLICATIONS

Maillard-Salina, et al., Physical evaluation of a new patch made of a progestomimetic in a silicone matrix, International Journal of Pharmaceutics, vol. 199(1), 2000, pp. 29-38.

* cited by examiner

*Primary Examiner* — Susan Tran
(74) *Attorney, Agent, or Firm* — Lucas & Mercanti, LLP

(57) ABSTRACT

A composition for transdermal permeation and a preparation method are disclosed. The composition including meloxicam as an active ingredient and further including at least one permeation enhancing agent selected from the group consisting of a sorbitan fatty acid derivative, a polyglyceryl fatty acid derivative, a polyethylene glycol vegetable oil ester, a polyethylene glycol corn oil glyceride, and a polyethylene glycol almond oil glyceride and at least one acrylic polymer adhesive having a hydroxyl group or no functional group.

2 Claims, 1 Drawing Sheet

PREPARATION AND COMPOSITION OF MELOXICAM TRANSDERMAL DRUG DELIVERY SYSTEM

This application is a 371 of PCT/KR/2007/004569 filed on Sep. 20, 2007, which claims the benefit of Korean Patent Application No. 10-2006-0094007 filed on Sep. 27, 2006, the contents of each of which are incorporated herein by reference.

TECHNICAL FIELD

The present invention relates to a transdermal patch composition containing meloxicam as an active ingredient, which is a non-steroidal-anti-inflammatory and analgesic component, having an excellent anti-inflammatory effect, and a method for preparing the same.

BACKGROUND ART

Meloxicam, which is a non-steroidal-anti-inflammatory and analgesic component, exhibits excellent anti-inflammatory effect with a low therapeutic dose. However, a typical non-steroidal-anti-inflammatory and analgesic component generates gastrointestinal side effects. Therefore, the development in a meloxicam transdermal patch allows for avoiding of side effects and the first-pass metabolism at the liver after the oral administration. However, despite the excellent anti-inflammatory effect of the meloxicam, the transdermal permeation patch containing the meloxicam has not been developed at present, because of low solubility and skin permeation.

The present invention is a matrix type transdermal patch having an active ingredient dissolved or suspended in a polymeric substance, and contains meloxicam as the active ingredient. Korean Patent Laid-open Publication No. 0059365 describes that the transdermal permeation of an anti-inflammatory and analgesic drug can be improved using a concentration gradient. However, it is difficult to apply the concentration gradient to the drugs with very low solubility, such as meloxicam. Korean Patent Laid-open Publication No. 0049598 discloses a method for preparing a transdermal drug delivery system by dissolving meloxicam in dimethylsulfoxide and diethanolamine. However, there is a problem in the utilization, because dimethylsulfoxide is an extremely skin irritant. Korean Patent No. 0406576 discloses a method for improving piroxicam permeation by forming a salt with ethanolamines. However, it is known that the salt formation, in the case of meloxicam, does not contribute largely to the improvement of its permeation. Korean Patent No. 0332210 discloses a method for preparing a transdermal drug delivery system containing an anti-inflammatory and analgesic component using tromethamine as a solubilizer and an acrylic adhesive. However, there is a problem in that when an acrylic adhesive having a carboxyl group as a functional group, among acrylic adhesives is used, the skin permeation of meloxicam is greatly decreased, which is different from the other anti-inflammatory and analgesic drugs.

DISCLOSURE OF INVENTION

Technical Problem

The present inventors have intensively conducted researches on improving transdermal permeation to maximize the therapeutic effect. As a result, they have found that a composition of a transdermal drug delivery system, prepared by suspending meloxicam into an acrylic adhesive having a hydroxyl group or no functional group, or a mixture thereof, and adding an appropriate permeation enhancing agent therewith, is excellent in skin permeation and exhibits excellent skin permeation with a lower dose compared with the dose per unit area of a conventional patch. In addition, in the process of producing a patch, it is difficult to suspend the drug due to a low solubility of meloxicam. However, by dissolving the meloxicam in dimethylformamide, the resulting solution is relatively easily volatilized, thereby evenly suspending the meloxicam into a matrix.

Therefore, the present invention has been made in view of the above problems, and it is an object of the present invention to provide a composition of a meloxicam transdermal drug delivery system to overcome the low solubility of meloxicam and maximize the skin permeation of meloxicam from a matrix, and a method for preparing the composition.

Technical Solution

In accordance with an aspect of the present invention, the above and other objects can be accomplished by the provision of a meloxicam transdermal patch comprising at least one permeation enhancing agent selected from the group consisting of a sorbitan fatty acid derivative, a polyglyceryl fatty acid derivative, a polyethylene glycol vegetable oil ester, a polyethylene glycol corn oil glyceride, and a polyethylene glycol almond oil glyceride, and at least one acrylic polymer having a hydroxyl group or no functional group as an adhesive.

In accordance with another aspect of the present invention, there is provided a method for preparing a meloxicam transdermal patch comprising dissolving meloxicam in dimethylformamide, adding at least one permeation enhancing agent selected from the group consisting of a sorbitan fatty acid derivative, a polyglyceryl fatty acid derivative, a polyethylene glycol vegetable oil ester, a polyethylene glycol corn oil glyceride, and a polyethylene glycol almond oil glyceride thereto, adding an adhesive solution containing an acrylic polymer having a hydroxyl group or no functional group thereto, applying and drying the mixed solution on a liner coated with silicone to form an acrylic adhesive layer, and laminating the acrylic adhesive layer onto a backing layer.

The present invention will be described in greater detail.

Meloxicam exists as zwitterions having two pKa values (pKa1=1.09, pKa2=4.18), and exhibits low skin permeation due to a high melting point and low solubility. Thus, in order to increase the skin permeability, a permeation enhancing agent is inevitably used. The meloxicam has very low solubility to the mostly known volatile solvents. Thus, dimethylformamide, although it is not an easily volatizing solvent, among the solvents with high meloxicam solubility is used to dissolve the medication. Dimethylsulfoxide or dimethylacetamide may also be used to dissolve the medication, but these solvents have relatively high boiling points. Thus they are disadvantageous over dimethylformamide.

In the meloxicam transdermal patch of the present invention, the meloxicam as an active ingredient is contained in an amount of 1 to 20% by weight based on an amount of the total composition.

Moreover, as the acrylic adhesive polymer used in the present invention, it is preferable that an acrylic polymer having a hydroxyl group or no functional group is used alone or in a combination of two or more. Examples of the acrylic adhesive polymer having a hydroxyl group include Durotak® 87-2510, Durotak® 87-2516, or Durotak® 87-2287 manufactured by National Starch and Chemical Company, or Gelva® 787 or Gelva® 737 manufactured by Monsanto Company. Examples of the acrylic adhesive polymer having no functional group include Durotak® 87-900A or Durotak® 87-9301 manufactured by Starch and Chemical Company. An acrylic polymer having a carboxyl group has a problem in that the skin permeability of meloxicam from the acrylic polymer is low due to its interaction with meloxicam. Such a problem is exhibited in the similar manner as for piroxicam, but it is not the case for a piroxicam salt. In the case of piroxicam, its salt form exhibits higher permeation than the piroxicam itself. On the contrary, in the case of meloxicam, the meloxicam itself exhibits higher permeation than its salt form. The acrylic polymer is contained in a range of 50 to 95% by weight based on an amount of the total composition for constituting the base layer, and preferably 60 to 90% by weight. When the amount of the acrylic polymer is less than 50% by weight, the adhesiveness is reduced. When the amount exceeds 95% by weight, the amount of the active ingredient is decreased so that no further excellent adhesiveness can be expected. A thickness of the base layer after drying is 10 to 300 μm, and preferably 40 to 200 μm. When the thickness is less than 10 μm, the medication dose contained per a unit area is too small, thus it is not effective. When the thickness exceeds 300 μm, the amount that permeates through skin is not increased any more, and the base layer may be pushed out of the backing layer when applied onto a joint area such as a knee. As the permeation enhancing agent that can be added to improve the skin permeation of the active ingredient, a sorbitan fatty acid derivative, a polyglyceryl fatty acid derivative, a polyethylene glycol vegetable oil ester, a polyethylene glycol vegetable oil glyceride, or the like can be used. Particularly preferably, sorbitan monooleate (Span® 80) as the sorbitan fatty acid derivative, polyglyceryl-6 oleate (Plural oleique®) as the polyglyceryl fatty acid derivative, or polyethylene glycol-12 palm kernel glyceride (Crovol® PK40) or polyethylene glycol-20 almond oil glyceride (Crovol® A40) as the polyethylene glycol vegetable oil glyceride can be used. Further, corn oil polyethylene glycol-8 ester (Labrafil® 2609) as the polyethylene glycol vegetable oil ester can be used. Such a permeation enhancing agent is used alone or in a combination of two or more, and is contained in an amount of I to 40% by weight, preferably 5 to 30% by weight, based on the total composition for constituting the matrix layer. When the permeation enhancing agent is used less than 1% by weight, there is no improving the effect of the skin permeation. When an exceeding amount of 40% by weight is used, the adhesiveness is reduced, and it is difficult to preserve the matrix form.

As the backing in the present invention, a polymeric film readily well known in the field of the transdermal delivery system such as polyester, polypropylene, polyethylenevinyl acetate, or polyurethane can be used. The film used as the backing should be impermeable to the active ingredient, and may be permeable or impermeable to air or moisture. As the liner, a widely known commercialized product such as a silicon-coated polyethylene film or a fluorocarbon diacrylate coating paper may be used. When releasing the liner from the patch, it should be easily removed without having residual matrix on the liner.

The matrix is mainly composed of an active ingredient, an acrylic adhesive and a solubilizer, a permeation enhancing agent, a crystallization inhibitor, and a moisturizer, and if necessary, a skin irritation preventing agent or a plasticizer may be added. As the solubilizer, a variety of alkalization agents may be used. Particularly preferably, monoethanol amine or diethanol amine may be used alone or in a combination of two or more. The solubilizer may be used in an equivalent ratio of 5 to 100% of meloxicam.

DESCRIPTION OF DRAWINGS

The above and other objects, features and other advantages of the present invention will be more clearly understood from the following detailed description taken in conjunction with the accompanying drawings, in which.

BEST MODE

Figure 1:
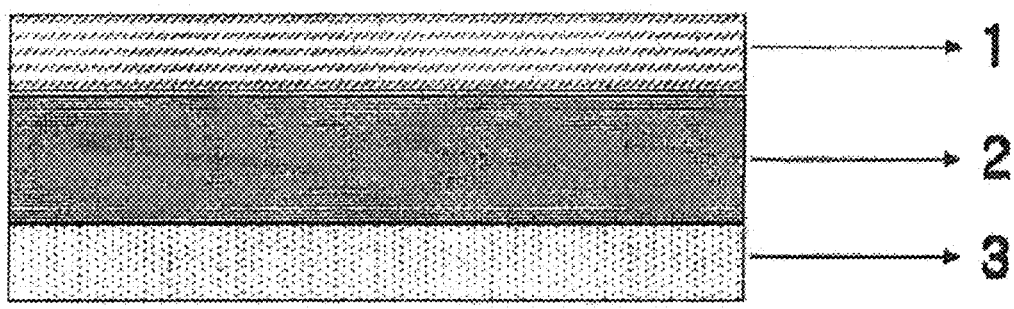
FIG. 1 is a diagram illustrating the structure of a transdermal permeation patch of the present invention.

Hereinafter, the present invention will be described in greater detail with respect to Examples, but is in no way meant as a limitation thereon.

Example 1

50 mg of meloxicam was dissolved in 1 ml of dimethylformamide, and 362 μl of sorbitan monooleate (Span® 80) was added thereto. The mixture was stirred until it was completely blended. To this solution, 3.27 g of an acrylic adhesive solution containing 1.4 g of an acrylic polymer (Durotak® 2516 manufactured by National Starch and Chemical Co.) was added and stirred for 10 minutes. The solution was applied onto a liner coated with silicon to have a thickness after drying of 160 μm. The coated liner was dried at 80° C. for 30 minutes and 110° C. for 15 minutes, sequentially. After drying, the acrylic adhesive layer was laminated onto a backing layer with pressure to prepare a patch.

Example 2

A patch was prepared in the same manner as in Example 1, except that polyglyceryl-6 oleate (Plural Oleique®) was used instead of sorbitan monooleate (Span 80).

Example 3

A patch was prepared in the same manner as in Example 1, except that polyethylene glycol-12 palm kernel glyceride (Crovol® PK40) was used instead of sorbitan monooleate (Span 80).

Example 4

A patch was prepared in the same manner as in Example 1, except that acrylic adhesives Durotak® 2516 (solid content=42.84%) and Durotak® 9301 (solid content=37.3%) were added in the amounts of 2.61 g and 0.75 g (ratio of 4:1), respectively, instead of 3.27 g of Durotak® 2516.

Example 5

A patch was prepared in the same manner as in Example 1, except that acrylic adhesives Durotak® 2516 (solid content=42.84%) and Durotak® 9301 (solid content=37.3%) were added in the amounts of 2.18 g and 1.25 g (ratio of 2:1), respectively, instead of 3.27 g of Durotak® 2516.

Example 6

A patch was prepared in the same manner as in Example 1, except that acrylic adhesives Durotak® 2516 (solid content=42.84%) and Durotak® 9301 (solid content=37.3%)

were added in the amounts of 1.09 g and 2.5 g (ratio of 1:2), respectively, instead of 3.27 g of Durotak® 2516.

Comparative Example 1

50 mg of meloxicam was dissolved in 1 ml of dimethylformamide. To this solution, 4.11 g of an acrylic adhesive solution containing 1.726 g of an acrylic polymer (Durotak® 2516 manufactured by National Starch and Chemical Co.) was added and stirred for 10 minutes. The solution was applied onto a liner coated with silicon to have a thickness after drying of 160 µm. The coated liner was dried at 80° C. for 30 minutes and 110° C. for 15 minutes, sequentially. After drying, the acrylic adhesive layer was laminated onto a backing layer with pressure to prepare a patch.

Comparative Example 2

A patch was prepared in the same manner as in Example 1, except that an acrylic adhesive Durotak® 2677 having a carboxyl group was added instead of 3.27 g of Durotak® 2516.

Comparative Example 3

A marketed product containing piroxicam (TRAST)

Comparative Example 4

A patch was prepared in the same manner as in Example 4, without adding sorbitan monooleate (Span 80).

Experimental Example 1

In order to find a degree of skin permeation for the prepared meloxicam patches, hairless mouse skin was used. Here, a marketed product TRAST containing piroxicam, which is related to meloxicam, was used as a comparative example. A hairless mouse skin (age of 6 to 8 weeks) was stripped approximately before the experiment, and a product to be tested was attached onto the skin by cutting the product in a circular shape to have a surface area of 2 cm². Then, the skin was fixed with a clamp to a flow-through diffusion cell, and the test samples were obtained for 28 hours in every 4 hours. The test samples were quantitated using a high performance liquid chromatography (HPLC). From these values, the permeation amounts of the medication were calculated. The results are presented in Table 1. To a receptor cell, an isotonic phosphate buffer solution (pH 7.4) was added and stirred uniformly using a magnetic stirrer while maintaining the temperature at 37° C. The analytic conditions are as follows.
<Analytic Conditions>
Column: Luna C8 (4×150 mm)
Mobile Phase: Methanol/Water/Phosphoric Acid (700:299:1)
Detector: UV 320 nm
Flow Rate: 1 ml/min

TABLE 1

|  | Skin Permeation (µg/cm²/hr) |
| --- | --- |
| Example 1 | 3.91 |
| Example 2 | 2.64 |
| Example 3 | 2.25 |
| Example 4 | 5.88 |
| Example 5 | 4.27 |
| Example 6 | 3.76 |
| Comparative Example 1 | 0.60 |

TABLE 1-continued

|  | Skin Permeation (µg/cm²/hr) |
| --- | --- |
| Comparative Example 2 | 1.9 |
| Comparative Example 3 | 1.22 |
| Comparative Example 4 | 0.58 |

As can be seen from Table 1, it is known that in the case of containing at least one acrylic polymer having a hydroxyl group or no functional group selected from a vinylacetate-acrylate copolymer or acrylate as an adhesive, a high permeation is exhibited. The permeation is not satisfactory for Comparative Examples 1 to 4. Especially, the permeation in Examples exhibited were much more excellent even when compared with the marketed product containing piroxicam (Comparative Example 3). Particularly, Examples 4 and 5 using a mixture of Durotak® 2516 (solid content=42.84%) and Durotak® 9301 (solid content=37.3%) in a ratio of 4:1 or 2:1, respectively, exhibited the most excellent effect.

Experimental Example 2

Adhesiveness of the prepared meloxicam patches according to the present invention and the marketed product TRAST were measured using an auto peeling tester. As a test substrate, a stainless steel or plastic plate was used. However, the patches came off too easily on the stainless steel plate and the patches did not come off easily on the plastic plate. Thus, it was impossible to compare each other. As a result, the comparison was carried on an actual human skin. Each patch was cut into 1 cm×5 cm, and about 3 cm of the patch was attached by gently pressing onto the skin using a thumb for 20 seconds. Then, from an angle of 90°, the patch was peeled off at a rate of 300 rpm and measured. The results are presented in Table 2 [see D. G, Maillard-Salinet al. International Journal of Pharmaceutics. 199 (2000) 29-38].

TABLE 2

|  | Adhesiveness (Kgf) |
| --- | --- |
| Example 4 | 0.33 |
| Example 5 | 0.27 |
| Example 6 | 0.26 |
| Comparative Example 3 | 0.18 |

As can be seen from Table 2, it is known that the adhesiveness of Example 4 to 6 are also more excellent compared with the marketed product containing piroxicam.

Experimental Example 3

The skin permeation of the prepared meloxicam patches of the present invention and the marketed product TRAST were compared, and to find the efficacy of the permeation enhancing agent, the patches of Example 4, Comparative Example 3, and the marketed product TRAST were cut into 10 cm², respectively. Each patch was attached to a rat skin, and blood after a certain time was obtained to compare the concentration of medication in blood plasma (see FIG. 2).

Figure 2:
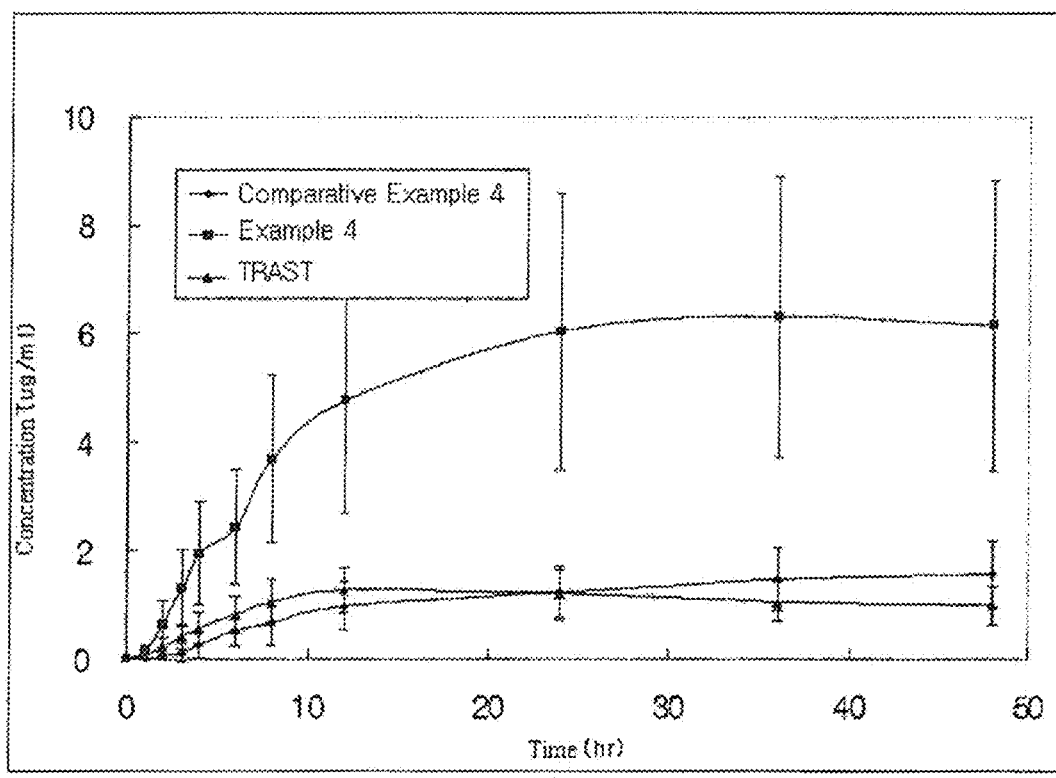
FIG. 2 is a comparison of a blood plasma level of meloxicam with respect to time after adhering a meloxicam patch of the present invention and a marketed TRAST patch onto skin.

As seen from the results of FIG. 2, Example 4 exhibited a greater concentration of medication in blood plasma compared with Comparative Example 4 or TRAST.

INDUSTRIAL APPLICABILITY

The meloxicam transdermal patch of the present invention avoids side effects and the first-pass metabolism at liver after the oral administration. Additionally, by improving the problem of low skin permeation during the administration of meloxicam through skin, it is expected to maximize the therapeutic effect of the meloxicam and minimize its side effects.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A meloxicam transdermal patch consisting essentially of:
   a sorbitan fatty acid derivative as a permeation enhancing agent in an amount of 21.54 to 40% by weight;
   at least one acrylic polymer having a hydroxyl group or no functional group as an adhesive in an amount of 50 to 95% by weight; and
   meloxicam in an amount of 1 to 20% by weight,
   wherein the meloxicam transdermal patch is prepared by:
      dissolving meloxicam in dimethylformamide;
      adding a sorbitan fatty acid derivative as a permeation enhancing agent;
      adding an adhesive solution containing an acrylic polymer having a hydroxyl group or no functional group thereto;
      applying and drying the mixed solution on a liner coated with silicone to form an acrylic adhesive layer; and
      laminating the acrylic adhesive layer onto a backing layer.

2. The patch according to claim 1, wherein the sorbitan fatty acid derivative is sorbitan monooleate (Span 80).

* * * * *